(12) United States Patent
Bettenga

(10) Patent No.: US 9,763,682 B2
(45) Date of Patent: Sep. 19, 2017

(54) SURGICAL GUIDES

(75) Inventor: Mason James Bettenga, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/814,395

(22) PCT Filed: Aug. 12, 2011

(86) PCT No.: PCT/US2011/047670
§ 371 (c)(1),
(2), (4) Date: May 24, 2013

(87) PCT Pub. No.: WO2012/021857
PCT Pub. Date: Feb. 16, 2012

(65) Prior Publication Data
US 2013/0245631 A1    Sep. 19, 2013

Related U.S. Application Data

(60) Provisional application No. 61/373,650, filed on Aug. 13, 2010, provisional application No. 61/374,053, (Continued)

(51) Int. Cl.
*A61B 17/58* (2006.01)
*A61B 17/60* (2006.01)
(Continued)

(52) U.S. Cl.
CPC ...... *A61B 17/1746* (2013.01); *A61B 17/1666* (2013.01); *A61B 17/1659* (2013.01); *A61B 17/1697* (2013.01); *A61B 2017/568* (2013.01)

(58) Field of Classification Search
CPC ............ A61B 17/1666; A61B 17/1746; A61B 17/1742; A61B 17/17
(Continued)

(56) References Cited

U.S. PATENT DOCUMENTS 4,528,980 A    7/1985  Kenna
5,951,605 A    9/1999  Dennis et al.
(Continued)

FOREIGN PATENT DOCUMENTS

CN    101711695 A    5/2010
EP       2168507 A2    3/2010
(Continued)

OTHER PUBLICATIONS

Japanese Office Action; Japanese Patent Office; Japanese Application No. 2013-524258; Jul. 13, 2015; 5 pages.
(Continued)

*Primary Examiner* — Kevin T Truong
*Assistant Examiner* — Si Ming Ku
(74) *Attorney, Agent, or Firm* — Taft Stettinius & Hollister LLP

(57) ABSTRACT

A surgical guide can include a first portion comprising an outer surface configured to conform to a portion of an acetabulum of a particular patient. The first portion can be configured to accommodate the ligamentum teres of the patient. The surgical guide can be configured to receive a second portion that includes an alignment portion defining an alignment axis such that when the surgical guide is coupled to the acetabulum, the alignment axis is oriented at a predetermined orientation relative to the acetabulum. The second portion can include a depth-limiting feature configured to limit insertion of a guide rod along the axis to a patient-specific insertion depth.

33 Claims, 7 Drawing Sheets

Related U.S. Application Data filed on Aug. 16, 2010, provisional application No. 61/461,096, filed on Jan. 13, 2011, provisional application No. 61/480,552, filed on Apr. 29, 2011.

(51) Int. Cl.
*A61F 2/00* (2006.01)
*A61B 17/17* (2006.01)
*A61B 17/16* (2006.01)
*A61B 17/56* (2006.01)

(58) Field of Classification Search
USPC ............ 606/91, 81, 86 R; 623/22.11, 22.12, 623/22.15, 22.21, 22.22, 19.11–19.13
See application file for complete search history.

(56) References Cited

U.S. PATENT DOCUMENTS

| | | | |
|---|---|---|---|
| 5,976,148 A * | 11/1999 | Charpenet | A61F 2/34 606/100 |
| 7,462,180 B2 * | 12/2008 | Raugel et al. | 606/91 |
| 2005/0107799 A1 | 5/2005 | Graf et al. | |
| 2007/0198022 A1 * | 8/2007 | Lang et al. | 606/88 |
| 2008/0009874 A1 | 1/2008 | Meridew et al. | |
| 2008/0009952 A1 * | 1/2008 | Hodge | A61B 17/1666 623/22.21 |
| 2009/0163922 A1 | 6/2009 | Meridew et al. | |
| 2010/0016984 A1 | 1/2010 | Trabish | |
| 2010/0082035 A1 | 4/2010 | Keefer | |
| 2010/0274253 A1 | 10/2010 | Ure | |
| 2011/0184419 A1 | 7/2011 | Meridew et al. | |
| 2011/0218545 A1 * | 9/2011 | Catanzarite | A61B 17/155 606/96 |
| 2011/0313424 A1 * | 12/2011 | Bono | A61B 17/1746 606/91 |

FOREIGN PATENT DOCUMENTS

| | | |
|---|---|---|
| JP | 60-108045 A | 6/1985 |
| JP | 2010-82448 A | 4/2010 |
| WO | 2008/005941 A2 | 1/2008 |

OTHER PUBLICATIONS

Chinese Patent Office, First Office Action dated Nov. 21, 2014, with translation, 20 pages.
Australian Patent Examination Report No. 1; Australian Patent Office; Australian Application No. 2011289173; May 29, 2015; 3 pages.
Chinese Search Report; Chinese Patent Office; Chinese Application No. 201180049421.8; Aug. 7, 2015; 4 pages.
Chinese Second Office Action; Chinese Patent Office; Chinese Application No. 201180049421.8; Aug. 17, 2015; 17 pages.
European Extended Search Report; European Patent Office; European Application No. 11817148.7; Apr. 4, 2016; 7 pages.
Canadian Office Action; Canadian Intellectual Property Office; Canadian Application No. 2,807,948; Feb. 8, 2017; 3 pages.
International Search Report; Korean Intellectual Property Office; International Application No. PCT/US2011/047670; Mar. 19, 2012; 4 pages.
Written Opinion of the International Searching Authority; Korean Intellectual Property Office; International Application No. PCT/US2011/047670; Mar. 19, 2012; 4 pages.

* cited by examiner

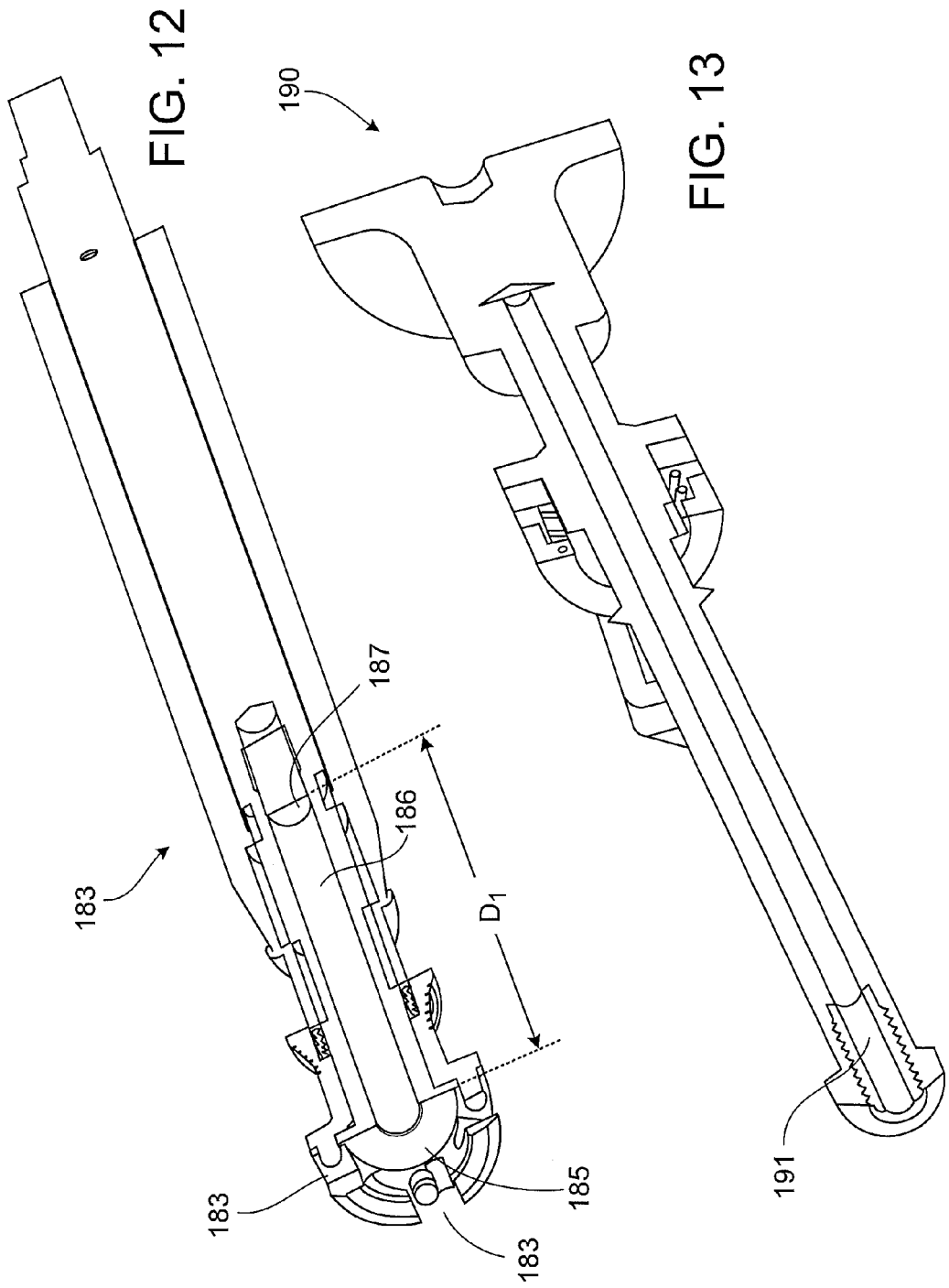

SURGICAL GUIDES

CROSS-REFERENCE TO RELATED APPLICATIONS

This application is a United States National Phase filing of International Application No. PCT/US11/047670 filed on Aug. 12, 2011 which claims priority to and the full benefit of U.S. Provisional Patent Application Ser. No. 61/373,650, filed Aug. 13, 2010, and titled "Method of Patient Specific Alignment Pin Placing for Acetabular Shell Alignment," U.S. Provisional Application Ser. No. 61/461,096, filed Jan. 13, 2011, and titled "Systems, Methods, and Devices for Facilitating Acetabular Surgical Procedures," U.S. Provisional Application Ser. No. 61/374,053, filed Aug. 16, 2010, and titled "Patient Specific Alignment Block for Placing an Acetabular Shell Alignment Pin," and U.S. Provisional Application Ser. No. 61/480,552, filed Apr. 29, 2011, and titled "Instrumentation Utilizing Patient-Matched Features," the entire contents of which are incorporated herein by reference.

TECHNICAL FIELD

This document relates to surgical guides.

BACKGROUND

A surgeon may use a variety of surgical instruments when performing a hip arthroplasty to implant a prosthesis such as an acetabular cup into a patient's acetabulum (or otherwise, when performing other orthopaedic surgeries to implant a prosthesis into a patient's anatomy). For example, the surgeon may use a reamer (or other cutting device) to mill out the acetabulum and thus form a socket within which an artificial cup can be anchored. An impactor may also be used to drive the cup into place within the acetabulum.

When operating, the surgeon must take care that the instruments are oriented as precisely as possible, so that the acetabular cup will ultimately be positioned and oriented as intended with the greatest possible precision. Otherwise, if the acetabular cup is not properly positioned (for example, if it has too shallow or too high of a cup inclination angle), the patient may experience excessive wear on the acetabular cup or components used with the acetabular cup. Other problems can include dislocation, impingement, limited ranges of motion, infection, or rejection of the implant. In addition, improper alignment may be more likely to occur if the surgeon performs the surgery freehanded.

Additionally, the surgeon must take care not to over-drill or over-ream the acetabulum. For example, in some surgical techniques, guide rods are inserted within the acetabulum to guide other surgical instruments (such as a reamer or an impactor) during the surgery. If the guide rod is inserted too deeply within the acetabulum, the guide rod can puncture or otherwise compromise the strength of the medial wall of the acetabulum, or injure other anatomy behind the acetabulum. Similarly, surgical instruments such as a reamer may ream too much (or too little) of the bone within the acetabulum.

SUMMARY

A surgical guide can include an outer surface that is at least in part conforms to a patient's anatomy. The surgical guide can engage the patient's anatomy at a desired location and/or orientation.

The surgical guide can include a portion configured to engage an acetabulum of a particular patient. The surgical guide can define an alignment axis relative to the acetabulum. The surgical guide can define a notch, slot, recess or groove such that the surgical guide mates with the acetabulum when ligaments of the hip are present.

The surgical guide can include a depth-limiting feature that limits the depth of a surgical procedure, such as drilling, reaming, or insertion of a guide rod, such as an alignment pin. The depth-limiting feature can impede over-drilling or over-reaming of the acetabulum. In some implementations, the depth-limiting feature can be a characteristic of a modular post of the surgical guide, for example, a predetermined and patient-matched height of the post. Surgical instruments for use with the surgical guide, such as drills, drivers, or reamers can have adjustable patient-matched mechanical stops to impede over-drilling or over-reaming.

According to one general aspect, a surgical guide includes a first portion including an outer surface configured to conform to a portion of an acetabulum of a particular patient. The first portion is configured to accommodate the ligamentum teres of the patient. The first portion is configured to receive a second portion that includes (i) an alignment portion defining an alignment axis such that when the surgical guide is coupled to the acetabulum, the alignment axis is oriented at a predetermined orientation relative to the acetabulum, and (ii) a depth-limiting feature configured to limit insertion of a guide rod along the axis to a patient-specific insertion depth.

Implementations may optionally include one or more of the following features. For example, the first portion defines a recess configured to admit the ligamentum teres. The first portion is substantially crescent-shaped. The first portion is dimensioned to not cover an acetabular fossa when engaged to the acetabulum. The first portion defines an opening through the first portion at a location that, when the first portion is coupled to the acetabulum, corresponds to the location of an acetabular fossa. The first portion includes walls defining a slot at a location that, when the first portion is coupled to the acetabulum, corresponds to the location of an acetabular notch. The slot spans the acetabular notch.

The outer surface is dimensioned to mate with the acetabulum in a single, predefined orientation. The second portion is detachable from the first portion and the second portion is configured to engage the first portion in a predefined orientation. The alignment portion includes a post defining a throughhole along the alignment axis. The depth-limiting feature is a patient-specific height of the post. The depth-limiting feature is configured to engage an instrument to impede insertion of the guide rod beyond the patient-specific insertion depth. The second portion includes a second outer surface dimensioned to conform to an anatomy of the patient. The depth-limiting feature is dimensioned to limit insertion of the guide rod from protruding through a medial wall of the acetabulum. The patient-specific insertion depth permits a secure engagement of the guide rod with cortical bone of the acetabulum.

According to another general aspect, a method includes: coupling a guide to a joint, the guide being customized for the anatomy of a particular patient; inserting a guide rod into the joint along an axis defined by the guide and to an insertion depth defined by the guide; removing the guide from the joint; and reaming a portion of the joint based on the position of the guide rod.

Implementations may include one or more of the following features. For example, reaming the portion of the joint based on the position of the guide rod includes reaming the portion of the joint such that a reaming depth is limited by engagement of a reamer with the guide rod. Reaming the portion of the joint based on the position of the guide rod includes reaming the portion of the joint along an axis defined by the guide rod. Inserting a guide rod into the joint along an axis defined by the guide and to an insertion depth defined by the guide includes engaging an instrument with a portion of the guide when a predetermined insertion depth is reached. Inserting a guide rod into the joint along an axis defined by the guide and to an insertion depth defined by the guide includes discontinuing driving the guide rod in response to engaging the instrument with a portion of the guide when a predetermined insertion depth is reached.

The guide includes a feature that engages a guide rod insertion instrument to limit the insertion depth of the guide rod. The guide includes an outer surface that substantially conforms to a portion of the patient's anatomy. The guide includes a first portion including the outer surface and a second portion detachable from the first portion, and the second portion includes a post that defines an aperture along the axis and engages a guide rod insertion instrument to limit the insertion depth of the guide rod. The guide includes a first portion that extends partially about a second portion of the guide, and removing the guide from the joint includes detaching the first portion from the second portion, removing the second portion from the joint, and removing the first portion from the joint after removing the second portion from the joint. Reaming a portion of the joint based on the position of the guide rod includes adjusting a reamer to set a maximum reaming depth for the patient.

According to another general aspect, a system includes: a guide conforming to a portion of a joint and defining an axis such that the axis has a predetermined position relative to the joint when the guide is coupled to the joint; an instrument configured to insert a guide rod into the joint along the axis such that engagement of the instrument with the guide limits an insertion depth of the guide rod; and a reamer configured to ream the joint such that engagement of the reamer with the guide rod limits a reaming depth relative to the joint.

Implementations may include one or more of the following features. For example, the reamer is configured to admit the guide rod and to ream the joint based on the alignment of the guide rod. The reamer is adjustable to set a reaming depth relative to the guide rod. The guide includes a first portion and a second portion detachable from the first portion. The first portion extends partially about the second portion and the second portion includes a post that defines an aperture along the axis. The post is configured to engage the instrument to limit the insertion depth of the guide rod. A height of the post is customized for a particular patient, and an end of the post is configured to engage the instrument. The instrument is configured to discontinue driving the guide rod in response to engagement with the guide. To discontinue driving the guide rod in response to engagement with the guide, the instrument is configured to reduce power to a driver coupled to the guide rod or to release a bit coupled to the guide rod from a driver.

The details of one or more implementations are set forth in the accompanying drawings and the description below. Other features, objects, and advantages will be apparent from the description and drawings, and from the claims.

DESCRIPTION OF DRAWINGS

FIG. 12 is a cross-sectional perspective view of a handle of a reamer.

FIG. 13 is a cross-sectional perspective view of an impactor.

Like reference symbols in the various drawings indicate like elements.

DETAILED DESCRIPTION

Figure 1:
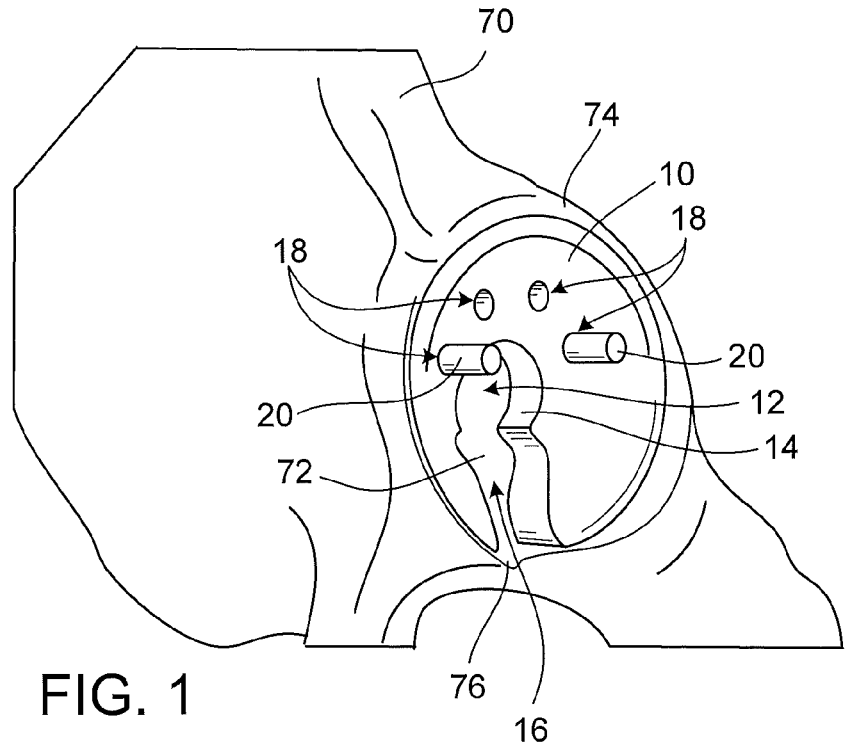
FIG. 1 is a perspective view of a surgical guide engaged with an acetabulum.
Figure 2:
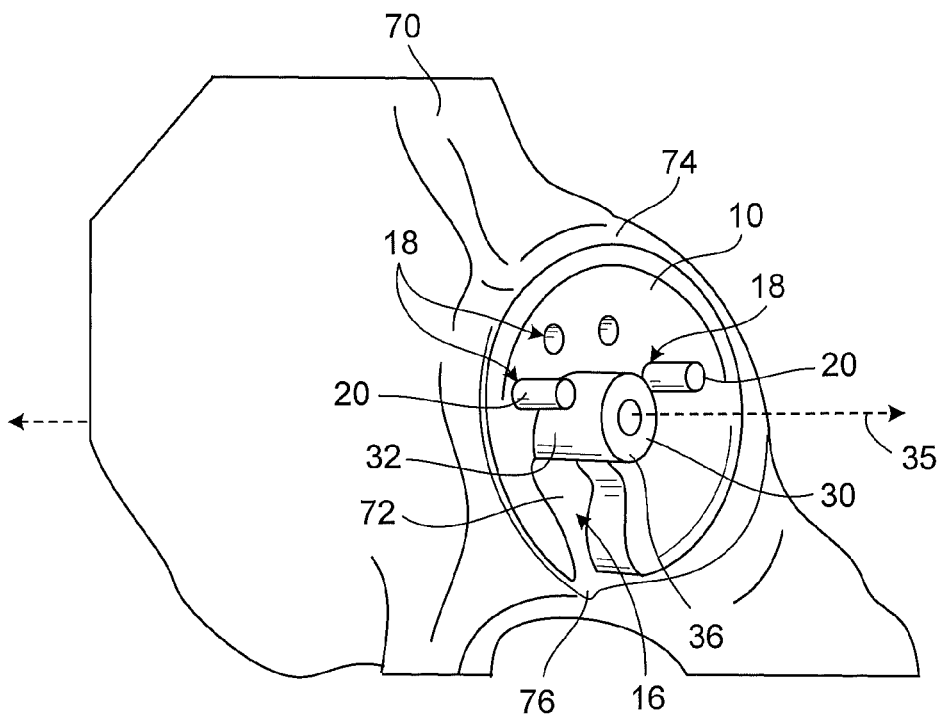
FIG. 2 is a perspective view of the surgical guide coupled to an alignment post.

Referring to FIGS. 1 and 2, a surgical guide 10 can be used to establish a surgical alignment relative to a joint of a patient. The surgical guide 10 can be customized for the anatomy of the patient. The surgical guide 10 can include patient-matched features that mate with the patient's anatomy in a predetermined orientation.

For arthroplasty of a hip joint, for example, the surgical guide 10, or a removable module such as a modular alignment post 30 (FIG. 2), can define an acetabular impaction axis relative to the acetabulum when engaged with the patient's anatomy. The surgical guide 10 or a removable module can also include patient-matched features that, for example, establish a patient-specific depth for inserting a guide rod or for reaming an acetabulum.

Although the techniques and devices described herein are generally configured for procedures on a patient's acetabulum, the techniques and devices may also be used in procedures on other portions of the anatomy, such as a femoral head, glenoid, humerus, radius, ulna, fibula, tibia, proximal femur, foot, ankle, wrist, extremity, or other bony or cartilaginous regions.

Features of a patient's anatomy can be indicated by imaging data acquired with magnetic resonance imaging (MRI), x-ray (including digital x-rays), ultrasound, computed tomography (CT), or other techniques. The imaging data can be processed to create a three-dimensional model of the patient's anatomy, and features of interest of the patient's anatomy can be identified. Based on the surfaces and contours indicated by the model, surfaces, contours, dimensions, and other characteristics of a device can be manufactured to match the patient's anatomy, as described further with respect to FIG. 14.

Figure 6:
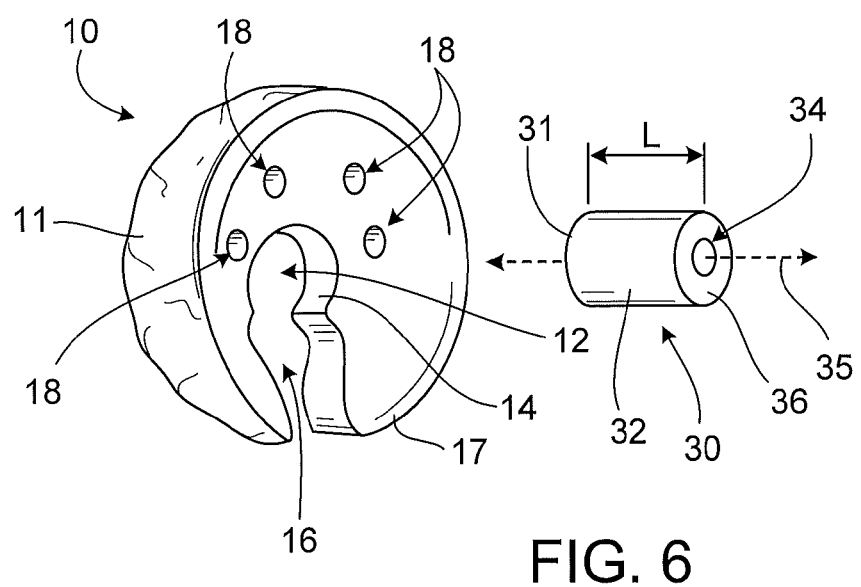
FIG. 6 is a perspective view of the surgical guide and the alignment post.

Referring to FIGS. 1 and 6, the guide 10 includes a patient-matched outer surface 11 that conforms to or substantially conforms to at least a portion of the patient's acetabulum 72. In the illustrated example, the geometry of the patient-matched surface 11 facilitates substantial conformance or otherwise fits to a particular patient's acetabulum 72 in substantially a unique position and/or orientation (e.g., in a single position, version, inclination, and/or other rotational position within the acetabulum 72). The patient-matched surface 11 need not extend continuously over the entire outer surface of the guide 10. Rather, only select portions of the outer surface may include the patient-matched surface 11. The patient-matched surface 11 can be textured to improve the overall stability of the guide 10 with respect to the patient's acetabulum 72. For example, the texturing may include serration, points, cross-hatch, grooves, ridges, bumps, or barbs that increase the friction between the patient's acetabulum 72 and the patient-matched surface 11.

The guide 10 can be dimensioned to be received substantially or entirely in the acetabulum 72. In some implementations, the guide 10 can extend beyond the acetabulum 72, and can include a patient-matched surface configured to conform to the other portions of the patient's pelvis 70, including, for example, an acetabular rim 74 and other non-articular surfaces of the pelvis 70. The guide 10 can also define one or more apertures 18 that can each receive a pin 20 or other fastener to secure the guide 10 to the acetabulum 72.

The guide 10 includes side walls 14 that define an aperture 12 and a slot 16. The aperture 12 can be defined through a generally central location of the guide 10. The slot 16 can be defined from the aperture 12 to an outer edge 17 of the guide 10, thus defining an open channel through the center of the guide 10 to the periphery or outer edge 17 of the guide 10. The guide 10 can thus be substantially crescent-shaped, with the outer edge 17 substantially unbroken except by the slot 16. As an alternative, for increased structural strength, a support structure can extend across the slot 16. For example, a support structure (not shown) can extend along the outer edge 17 such that the circumference of a rim of the guide 10 is unbroken.

The locations of the aperture 12 and the slot 16 can correspond to particular anatomical features when the guide 10 is mated with the acetabulum 72. For example, the aperture 12 and/or the slot 16 can be defined at a location corresponding to the ligamentum teres. The guide 10 can thus be dimensioned to accommodate the ligamentum teres of the patient when mated with the pelvis 70. The guide 10 can admit the ligamentum teres into the aperture 12, the slot 16, and/or a recess in the outer surface of the guide 10. As a result, a surgeon is not required to remove the ligamentum teres to insert the guide 10 into the acetabulum 72.

Similarly, guide 10 can be dimensioned such that when the guide 10 is mated with the acetabulum 72, the location of the aperture 12 and the slot 16 correspond to the location of the acetabulum fossa of the patient. The location of the aperture 12 and/or the slot 16 can cause the acetabulum fossa to be partially uncovered or substantially completely uncovered when the guide 10 is mated with the acetabulum 72. The walls 14 can also define the slot 16 at a location corresponding to the acetabular notch 76 of the pelvis 70. For example, the slot 16 can span the acetabular notch 76 when the guide 10 is mated with the acetabulum 72. In some implementations, an outer surface of the guide 10 (which may or may not be coextensive with the patient-matched surface 11) can extend at least 270 degrees about the center of the guide 10, with the slot 16 aligned at the acetabular notch 76.

The walls 14 defining the aperture 12 can be configured to receive the modular alignment post 30. The guide 10 and the alignment post 30 can be detachable. As an alternative to the modular post 30, the guide 10 and a post or other alignment feature can be formed as a single integral unit.

The post 30 may contact, but need not contact, the acetabulum 72. In some implementations, an end 31 of the post 30 includes a patient-matched surface that substantially conforms to a portion of the acetabulum 72. Thus, the end 31 of the post 30 can mate with the acetabulum 72 in a single position and/or orientation. The patient-matched surface of the post 30 can include geometry that sufficiently conforms to the patient's particular anatomy to establish a desired rotational position of the post 30 in the guide 10.

The walls 14 can include a mating structure to couple to the post 30 in a predetermined orientation. Thus, the position of the post 30 with respect to the patient's anatomy can be determined by the engagement of the post 30 with the guide 10. Additional or alternative structure can be provided to establish a desired rotational orientation of the post 30 relative to the aperture 12 and/or a desired depth of the post 30 in the aperture 12. For example, one or both of side walls 14 of the guide 10 and a side wall 32 of the post (or other structure associated therewith) may be structured, dimensioned, positioned and/or oriented to establish a depth of the post 30 in the aperture 12 and/or a rotational orientation of the post 30 relative to the aperture 12. The side walls 14 and 32 may include keying structures that interact to limit one or both of rotational orientation and depth of the post 30 along the aperture 12.

The post 30 can define an alignment axis 35 such that when the guide 10 and post 30 are coupled to the acetabulum 72, the alignment axis 35 is oriented at a predetermined orientation relative to the acetabulum 72. The post 30 can define an aperture 34 to receive a guide rod or drill bit for insertion within the acetabulum 72. The orientation of the aperture 34 may be determined pre-operatively based on patient-specific data such that it is collinear with the desired trajectory of the guide rod.

The post 30 can also include a depth-limiting feature configured to engage a surgical instrument to limit the depth that a guide rod is implanted into the acetabulum 72. The depth-limiting feature can be, for example, an end 36 of the post 30, which has a position relative to the acetabulum 72 set by a length, L, of the post 30. The end 36 of the post 30 can be configured to interact with a surgical instrument to limit reaming or drilling or insertion of a guide rod. For example, the end 36 can act as a mechanical stop that blocks an instrument, such as a driver for the guide rod, from advancing further. The end 36 can also engage a switch or other mechanism to terminate advancement of a surgical instrument.

The length, L, of the post 30 can be determined based on, for example, a desired drill depth determined for the specific patient, known characteristics of a guide rod to be inserted, and characteristics of instruments to be used. The desired insertion depth of the guide rod may be determined from the patient's bony anatomy, as indicated by a model determined using imaging data for the patient's pelvis 70. For example, the desired insertion depth can be selected to provide sufficient depth that the guide rod reaches a stable and secure engagement with cortical bone of the pelvis 70. In addition, the insertion depth can be selected so that the guide rod does not protrude through the medial wall of the acetabulum 72.

Figure 7:
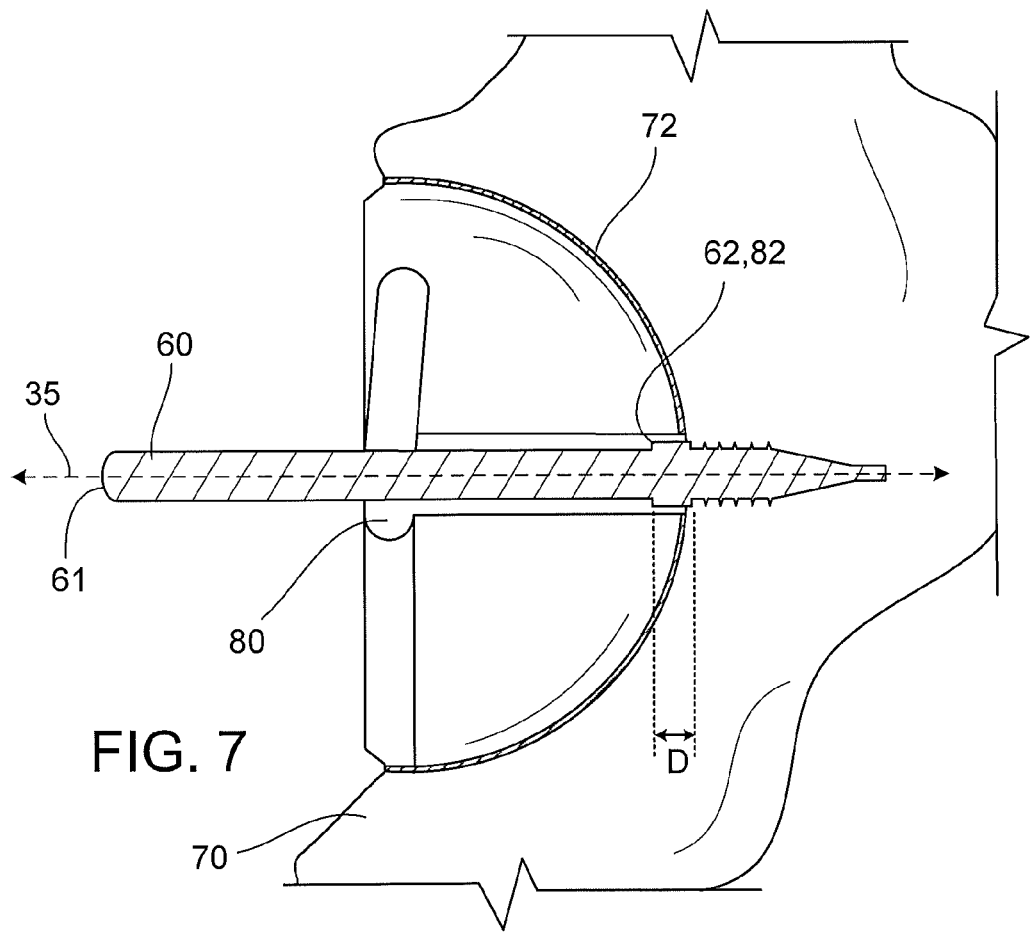
FIG. 7 is a cross-sectional side view of the guide rod inserted in the acetabulum, and a reamer dome coupled to the guide rod.

In some implementations, a feature of the guide rod can limit a reaming depth of the acetabulum 72 after installation of the guide rod (see FIG. 7). Thus, the desired reaming depth of the acetabulum 72 can also be considered in selecting the length, L.

The post 30 can be custom-fabricated to define a patient-specific insertion depth. Alternatively, the post 30 can be selected from a set of posts with standard sizes having incrementally varying lengths. The surgeon can thus select the post 30 that provides the appropriate length, L, for the patient to set a patient-specific insertion depth.

In some implementations, the depth-limiting feature can be a feature other than the position of the end 36 of the post 30 relative to the acetabulum 72. For example, the depth limiting feature can alternatively be a structure of the side wall 32 or a structure within the aperture 34. As an alternative, the depth-limiting feature may be a portion of the guide 10.

Referring to FIGS. 1 to 5, a surgeon can establish a predetermined surgical alignment using the guide 10 and the post 30. Referring to FIG. 1, the surgeon inserts the guide 10 into the acetabulum 72 and orients the guide 10 such that the guide 10 mates with the acetabulum 72. Because the guide 10 accommodates the ligamentum teres, the surgeon need not remove the ligamentum teres. The surgeon can then insert one or more pins 20 through the apertures 18 to secure the guide 10 to the acetabulum 72.

Referring to FIG. 2, the surgeon inserts the post 30 into the aperture 12 of the guide 10. The post 30 can be positioned in a stable predetermined position, for example, through engagement with the acetabulum 72 and/or engagement with the side walls 14 of the guide 10. In the predetermined position, the post 30 defines the alignment axis 35 for the surgical procedure and is dimensioned to limit insertion of a guide rod to a patient-specific depth.

In some implementations, the alignment axis 35 extends into the acetabular fossa, and thus the post 30 is positioned over the acetabular fossa. The post 30 and alignment axis 35 can alternatively be defined at a different portion of the acetabulum 72, and need not be centrally located.

Figure 3:
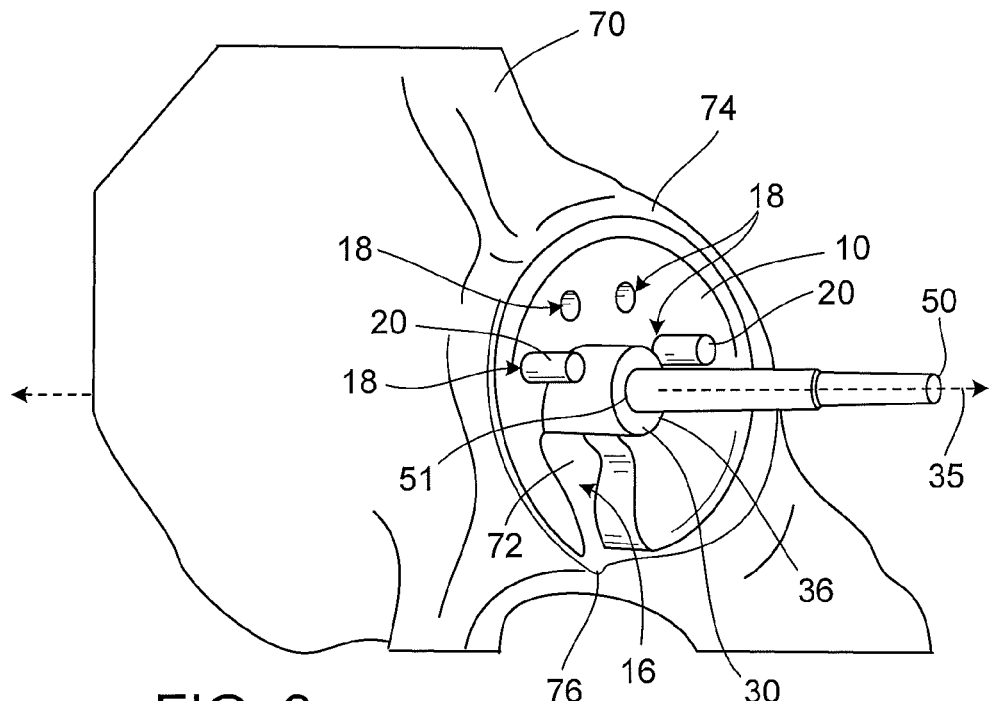
FIG. 3 is a perspective view of the surgical guide and the alignment post, shown with a driver.
Figure 4:
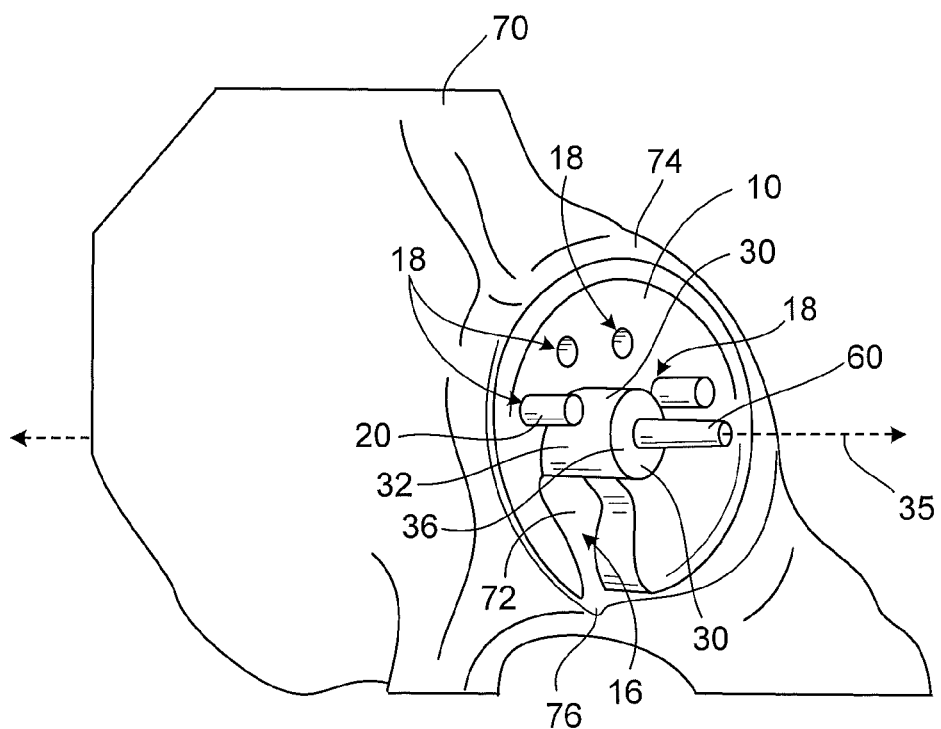
FIG. 4 is a perspective view of the surgical guide and the alignment post, shown with a guide rod installed in the acetabulum.

Referring to FIGS. 3 and 4, the surgeon inserts a guide rod 60 into the aperture 34 of the post 30, aligning the guide rod 60 along the alignment axis 35. The surgeon uses a driver 50 or other instrument to advance the guide rod into the acetabulum 72. The driver 50 may be any tool, whether powered or manual, that helps the surgeon advance the guide rod 60 into the acetabulum 72, or other portion of the patient's anatomy.

The guide rod 60 may be any rod, shaft, or pin that is inserted in the acetabulum 72 and protrudes at least some distance to thus serve as a guide for other surgical instruments. If desired, the guide rod 60 may have structure (such as threads) to engage with the bone in the acetabulum 72. In some implementations, the guide rod 60 is an elongated pin with threads on an end such that it can be rotationally driven into the acetabulum by a removable driver 50. The removable driver 50 and the guide rod 60 may both include structure for interacting with one another to translate rotational movement of the driver into rotational movement of the guide rod. For example, the guide rod 60 may include a shank with flattened portions for receipt in an appropriately shaped aperture in the driver 50 to couple the two structures together.

Once a shoulder 51 of the driver 50 contacts the end 36 of the post 30, the driver 50 cannot advance the guide rod 60 into the acetabulum 72 any further. Thus, the engagement of the driver 50 with the post 30 impedes over-drilling or excessively deep insertion of the guide rod. In addition, by inserting the guide rod 60 until the driver 50 engages the post 30, the surgeon can ensure that the guide rod 60 enters the anatomy sufficiently and reaches the preferred or patient-specific depth.

In some implementations, engagement of the driver 50 to the post 30 can disengage the pin from the driver to limit further insertion. As an alternative, the engagement with the post 30 can trigger a switch that cuts power to a motorized driver to limit further insertion.

Referring to FIG. 4, the driver 50 is removed, and the guide rod 60 is shown after being inserted at the desired drill depth into the acetabulum 72.

Figure 5:
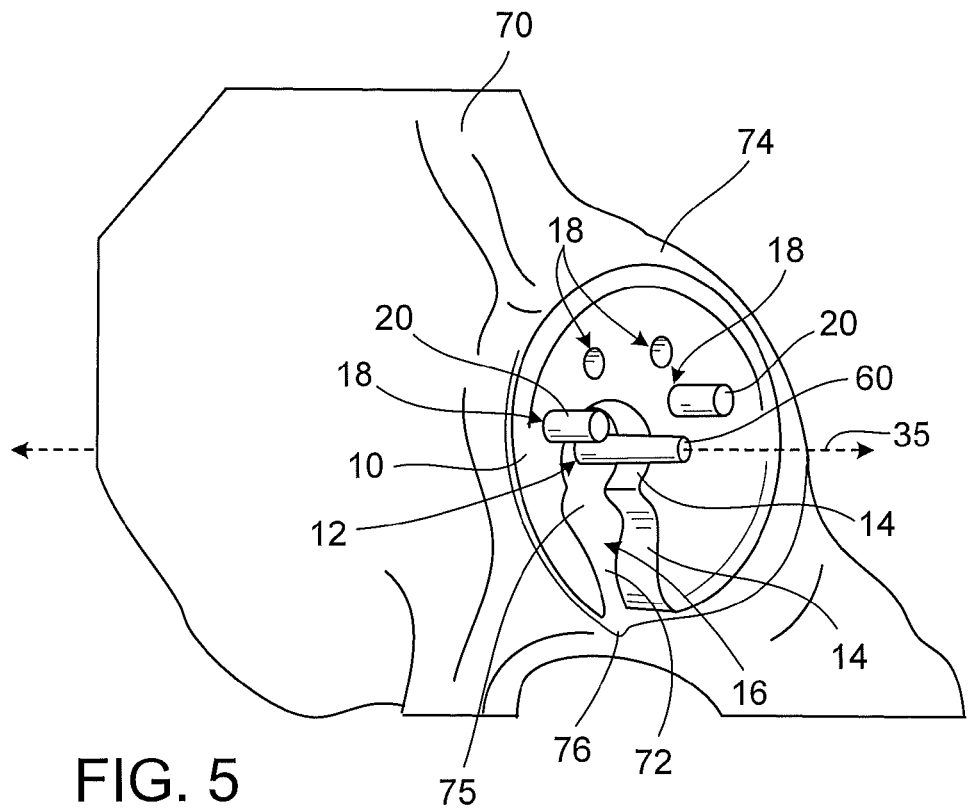
FIG. 5 is a perspective view of the surgical guide, shown with the guide rod.

Referring to FIG. 5, the post 30 can be removed from around or slid off of the guide rod 60, leaving the guide rod 60 in place. In some implementations, the rotational orientation of the post 30 relative to the guide 10 may affect the height of the post 30 relative to the patient's specific anatomy, and a patient-matched surface of the post 30 (e.g., at the end 31) may facilitate ensuring that the height of the post 30 when positioned on the patient's anatomy is consistent with a pre-surgical plan.

The surgeon can remove the guide 10 once the guide rod 60 is inserted within the acetabulum 72. The slot 16 defined by the guide 10 opens to the periphery of the guide 10. This opening facilitates removal of the guide 10 from the guide rod 60 without substantial risk of disturbing the position and/or orientation of the guide rod 60. The surgeon can manipulate the guide 10, if necessary, by, for example, moving it back and forth within the acetabulum 72 and the slot 16, without disturbing the guide rod 60. Further, the slot 16 and the aperture 12 facilitate removal of the guide 10 by reducing suction between the patient-matched surface 11 and the acetabulum 72.

The slot 16 is not required, and in some implementations, a guide may not define a slot 16. The surgeon can remove a guide without a slot 16 by pulling the guide 10 directly over the guide rod 60, with the guide rod 60 passing through the aperture 12. In such an implementation, a recessed portion of the outer surface of the guide or the patient-matched surface 11 can accommodate the ligamentum teres (e.g., corresponding to a location 75 of the pelvis 70).

Once the guide 10 is removed, the guide rod 60 remains in place to serve as a guide for other surgical instruments, which may also include patient-matched features to ensure that desired depths are maintained. For example, it may be desired to only ream a certain amount of bone from the acetabulum 72.

Figure 8:
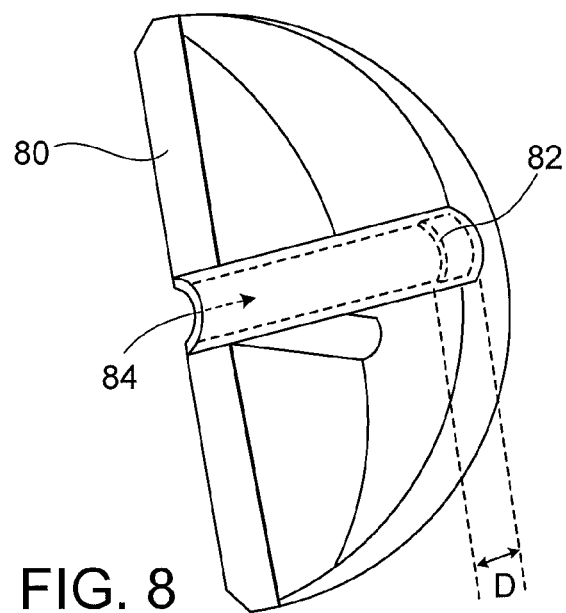
FIG. 8 is a perspective view of the reamer dome.

Referring to FIGS. 7 and 8, a reamer dome 80 may be provided that defines an aperture 84 to admit the guide rod 60. The reamer dome 80 may include a shoulder 82 with a distance, D, that is dimensioned to maintain the desired reaming depth. In use, a shoulder 62 on the guide rod 60 contacts the shoulder 82 of the reamer dome 80, impeding the reamer dome 80 from reaming the bony anatomy beyond the desired reaming depth. Additionally, the surgeon knows not to stop reaming until contact between the shoulders 62, 82 is reached. As an alternative, a portion of an instrument can engage an end 61 of the guide rod 60 (rather than the shoulder 62) to limit a depth of reaming. In some implementations, the length of the guide rod 60, the position of the shoulder 62 on the guide rod 60, the distance, D, of the reamer dome 80, and other parameters can be patient-matched.

In some implementations, standard instruments and/or guide rods can be used, and the patient-specific insertion depth can define a reaming depth. The insertion depth of the guide rod 60 can be adjusted (within an acceptable range indicated by the model of the patient's anatomy) such that the shoulder 62 or the end 61 is positioned at an appropriate position with respect to the patient's acetabulum 72 to set the preferred reaming depth.

FIGS. 9 to 13 show other devices that can be used to insert a prosthesis into the acetabulum 72 at desired depths and orientations.

Figure 9:
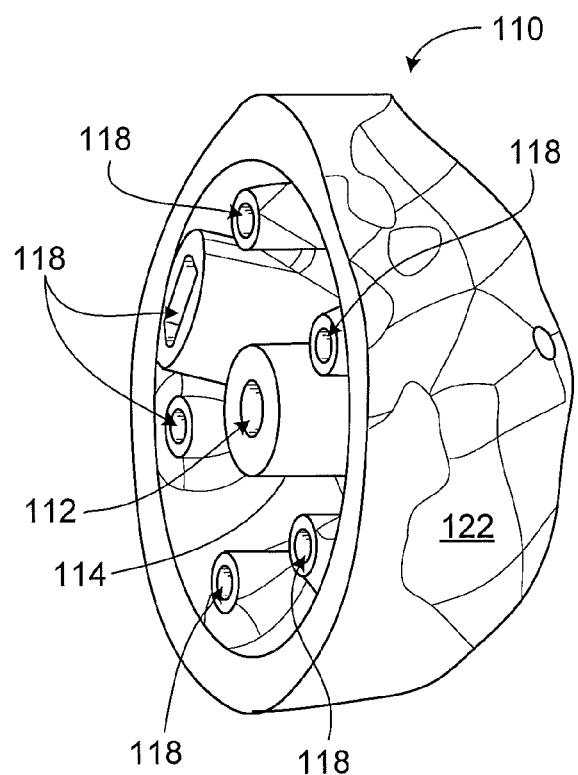
FIG. 9 is a perspective view of an alternative surgical guide.
Figure 10:
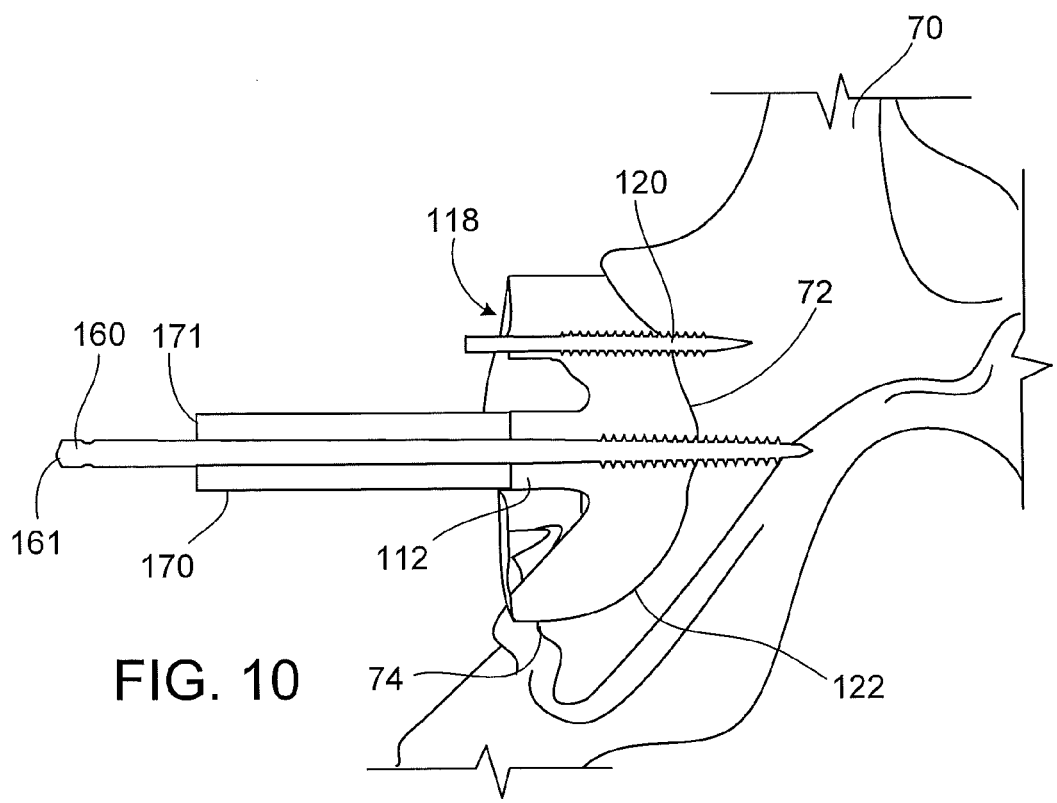
FIG. 10 is a cross-sectional side view of the surgical guide of FIG. 9, with a guide rod and a connector for use with a driver.
Figure 11:
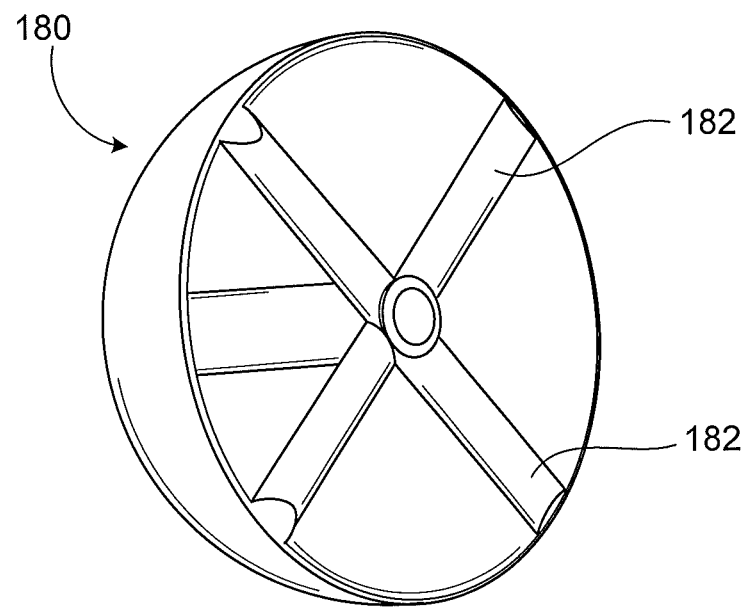
FIG. 11 is a perspective view of an alternative reamer dome.

Referring to FIGS. 9 and 10, a guide 110 is dimensioned to fit within a patient's acetabulum 72. In some implementations, at least a portion of the outer surface of the guide 110 includes a patient-matched surface 122 that substantially conforms to at least a portion of the patient's acetabulum 72. The patient-matched surface 122 may conform or otherwise fit to the acetabulum 72 in only one position and/or orientation, and can include features as described above for the patient-matched surface 11 of the guide 10.

If desired, the guide 110 may define apertures 118 dimensioned to receive pins 120 to secure the guide 110 to the acetabulum 72 (as shown in FIG. 10). Additionally, the guide 110 may define an aperture 112 through an extension 114 or other integral portion of the guide 110. The aperture 112 is dimensioned to receive a guide rod 160 to be inserted within the acetabulum 72. The orientation of the aperture 112 may be determined pre-operatively based on patient-specific data such that the aperture 112 is collinear with the desired trajectory of the guide rod 160. The guide rod 160 may be any rod, shaft, or pin that is inserted in the acetabulum 72 and protrudes at least some distance to thus serve as a guide for other surgical instruments. If desired, the guide rod 160 may have structure (such as threads or barbs) to engage with the bone in the acetabulum 72.

FIG. 10 is a cross-sectional view showing a guide rod 160 being inserted into the acetabulum 72. A connector 170 can be used with a driver (not shown) to ensure that the guide rod 160 is inserted at a desired drill depth within the acetabulum 72. The connector 170 for use with the driver may be provided with a length that is based on patient-specific data related to the desired drill depth of insertion. In other implementations, the connector 170 may be a standard length and its depth may be controlled by a post including an aperture defined using patient specific data. Once the driver makes contact with the end 171 of the connector 170, the driver cannot advance the guide rod 160 into the acetabulum 72 any further. Thus, the guide rod 160 will not be inserted in excess of (or less than) the desired drill depth. After the guide rod 160 is inserted, the connector 170 can be removed from the guide rod 160, the pins 120 can be removed from the guide 110, and the guide 110 can be removed from the acetabulum 72, thus leaving the guide rod 160 in place within the acetabulum 72.

The guide rod 160 serves as a guide for other surgical instruments, such as a reamer (FIGS. 11 and 12) or an impactor 190 (FIG. 13). Such other surgical instruments may also include patient-matched features to maintain desired depths. For example, a reamer dome 180 and handle 184 may be provided to ream the acetabulum 72. The reamer dome 180 may couple to the handle 184 in various ways. For example, the dome 180 can be provided with cross-bars 182 that are received within notches 183 at the end of the handle 184. The cross-bars 182 press down retractable pins 185 on the handle 184, and then the dome 180 is rotated with respect to the handle 184 such that the cross-bars 182 are received within undercuts on the notches 183. Other structures, such as threads, can alternatively be used.

Referring to FIG. 12, the reamer handle 184 defines a central aperture 186 that admits the guide rod 160. As the surgeon reams the acetabulum, the guide rod 160 advances within the aperture 186. Eventually, an end 161 of the guide rod 160 engages a surface 187 within the aperture 186, causing the reamer to "bottom out." When the guide rod 160 contacts the abutting surface 187, the surgeon is impeded from reaming the acetabulum 72 any further.

The length, $D_1$, of the aperture 186 may be based on the patient's imaging data. The reamer handle 184 can be adjustable to change the length, $D_1$. If the patient's acetabulum 72 should only be reamed to a particular depth, then the length, $D_1$, can be set based on the desired depth, taking into account, for example, the length of the guide rod 160 and the position of the guide rod 160 relative to the acetabulum 72. For example, when the guide rod 160 is installed at a known insertion depth and the guide rod 160 has a known length, the length, $D_1$, can equal the length of the guide rod 160 minus the insertion depth, plus the desired reaming depth. As an alternative to adjusting characteristics of a reamer, guide rods having patient-specific lengths can be used.

Referring to FIG. 13, a handle of an impactor 190 can define a central aperture 191 that admits the guide rod 160. The aperture 191 can be a throughhole that guides impaction along the axis of the guide rod 160, but does not bottom out against the end 161 of the guide rod 160. The impactor 190 can be configured to not strike the end 161 of the guide rod 160 during impaction, thus avoiding driving the guide rod 160 through the medial wall of the acetabulum 72 or damaging the cortical bone with which the guide rod 160 is engaged.

Accordingly, surgical techniques may be performed with the devices having patient-matched features described herein. For example, a surgeon dislocates a hip joint, creates an incision to access the joint, and inserts a guide into the acetabulum. The surgeon mates the patient-matched outer surface to the acetabulum such that the guide engages the acetabulum at the predetermined orientation.

When a central post is used (as in FIG. 2), the surgeon may also insert the post. Then the surgeon may use the guide to insert a guide rod within the acetabulum. Patient-matched features of the guide and/or post help ensure that the guide rod is only placed within the acetabulum to a certain pre-determined depth. Then the surgeon may remove the guide and/or post, leaving the guide rod secured within the acetabulum. Next, the surgeon may ream the acetabulum in order to prepare the acetabulum to receive an implant. If desired, the surgical tools used to ream the acetabulum may contain patient-matched features that engage with structure on the guide rod to help ensure that the acetabulum is reamed a desired amount. Next, the surgeon may implant a prosthesis within the acetabulum, and if desired, impact the prosthesis using an impactor.

Figure 14:
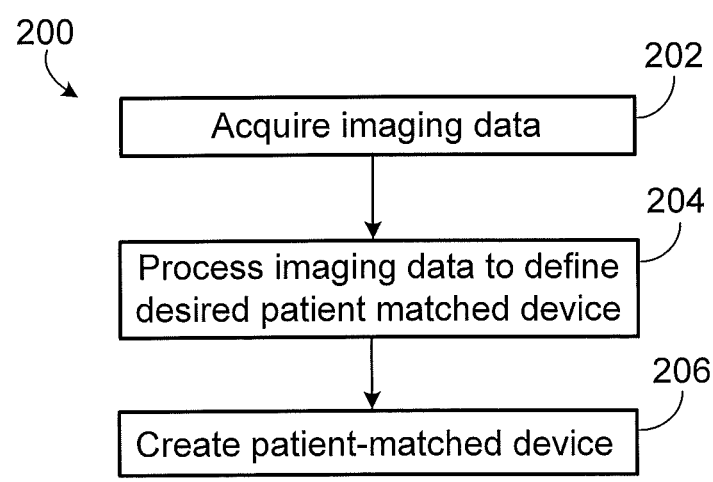
FIG. 14 is a flow diagram illustrating a process for making devices having patient-matched features.

Referring to FIG. 14, a process 200 can be used to create devices described herein having patient-matched features. The same general discussion relates to all of the patient-matched features (such as patient-matched surface 122 or any of the desired depths described herein).

The process 200 includes obtaining imaging data about the geometry or other aspects of the specific patient's anatomy (202). Imaging data can include data about the bone and/or cartilage surfaces of interest, or data sufficient to determine relevant mechanical axes or desired depths for reaming or drilling. The imaging data may be obtained with magnetic resonance imaging, x-ray (including digital x-rays), ultrasound, computed tomography (CT), or other techniques. For ease of reference, this disclosure refers generally to "imaging data," although in some implementations, non-image-based technologies could be used to obtain sufficient data about the anatomy of interest. In some implementations, the imaging data does not relate to the entire portion of the anatomy of interest (e.g., the entire acetabulum), but instead, only relates to certain key or desired anatomical points or areas (e.g., the medial portion of the acetabulum).

The imaging data may be processed to define the properties of patient-matched device (204), including defining contours of surfaces dimensioned to conform to portions of the patient's anatomy. The term "patient-matched device" is used generally to refer to any of the devices described herein having patient-matched features. Processing the imaging data can include, for example, creating a three-dimensional model of the patient's anatomy and identifying desired position(s), orientation(s), or depth(s) of instruments and/or implants with respect to the patient's anatomy. Processing the imaging data can also include designating alignment axes, cutting planes, or other constructs or references. In some implementations, the patient-matched device or a portion thereof is automatically (e.g., programmatically) defined based on the three-dimensional model, the designated reference data, and other inputs, such as a "blank" from which the patient-matched device is defined.

A surgical alignment axis or other surgical alignment for a particular patient can be defined relative to the three-dimensional model of the patient's anatomy. The patient-matched devices described above can be formed to define the surgical alignment axis relative to the patient's anatomy. During surgery, the patient-matched devices can indicated the location and orientation of the desired surgical alignment relative to the patient's anatomy, for example, when the devices are mated to the patient's acetabulum.

To define the surgical alignment axis relative to the model, the position of an anatomical reference frame for the patient can be determined relative to the model. For example, an alignment of an imaging device used to acquire imaging data, for example, an MRI scanner or a CT scanner, can be used as an approximation of an anatomical reference frame. If the patient lies on an MRI table flat on his or her back, for example, a plane parallel to the table lies generally in the coronal plane of the patient. The sagittal plane extends orthogonal to the table, along the length of the table, and the transverse plane is orthogonal to the coronal plane and the sagittal plane.

As an alternative, anatomical landmarks can be identified in the model, and anatomical reference frame can be defined based on the locations of the landmarks. For example, a sagittal plane for the patient can be defined through one or more of, a point corresponding to the lumbar spine, a point corresponding to the pubic symphysis, and a point corresponding to the coccyx. A pubis-ilium axis can be defined through points corresponding to the pubic symphysis (or the anterior tip of the crest of the pubis) and the anterior tip of the anterior-superior spine of the ilium. The coronal plane can be defined to be orthogonal to the sagittal axis and to include intersect the pubis-ilium axis. A transverse plane can be defined orthogonal to the sagittal plane and the coronal plane.

After an anatomical reference frame is determined for the model, the alignment axis can be defined relative to the anatomical reference frame. The orientation of the alignment axis can be defined such that installation of an acetabular cup into the acetabulum along the alignment axis results in a desired inclination angle and/or anteversion angle of the acetabular cup relative to the patient's anatomy. The alignment axis can have an orientation perpendicular to a plane that represents the face of the acetabular cup in its installed position. The inclination angle and anteversion angle for the acetabular cup can be determined for the particular patient.

The alignment axis can be defined to intersect a center of motion for the patient's hip joint. The center of rotation can be determined as, for example, the center of a best-fit sphere that approximates the surface of the acetabulum. The center of rotation can be determined by data fitting a sphere to the surface of the acetabulum of the model, and identifying the center of the sphere.

In some implementations, rather than determining the orientation of the alignment axis relative to an anatomical reference frame for the patient, the orientation of the alignment axis can be defined as an orientation perpendicular to the acetabular rim of the model. A best-fit plane can be generated that intersects points on the acetabular rim of the model. The alignment axis can then be defined to be perpendicular to the best-fit plane and to intersect the center of the best-fit sphere.

In some implementations, one or more of the above described operations can be performed using computer equipment, whether as a single device or a networked system. Such computer equipment, can include one or more storage devices, one or more processors, and subsystems providing input and output interfaces, which can facilitate performing at least some of the above identified steps, including creating one or more models. One or more of the above described steps could be performed using a computer assisted design (CAD) software package or another type of design software package.

The process 200 can include creating or manufacturing the patient-matched device (206). Examples of technologies that can be used to manufacture the device include, for example, machining, three-dimensional printing, selective laser sintering, and molding processes.

A number of implementations have been described. Nevertheless, it will be understood that various modifications may be made without departing from the spirit and scope of the invention. Accordingly, other implementations are within the scope of the following claims.

What is claimed is:

1. A surgical guide comprising:
   a crescent-shaped first portion comprising a first outer surface and a second outer surface that meets the first outer surface at an outer edge, the first outer surface including a patient-matched outer surface configured to conform to a portion of an acetabulum of a particular patient, the second outer surface including a crescent-shaped planar surface having a slot defined therein to accommodate a ligamentum teres mated with a pelvis of the particular patient; and
   a second portion, the first portion having walls that define an aperture extending through the first portion to receive the second portion, the second portion comprising (i) an alignment portion defining an alignment axis such that when the surgical guide is coupled to the acetabulum, the alignment axis is oriented at a predetermined orientation relative to the acetabulum, and (ii) a depth-limiting feature configured to limit insertion of a guide rod along the axis to a patient-specific insertion depth, wherein the aperture is defined at an end of the slot opposite the outer edge, and the aperture extends from the first outer surface to the second outer surface.

2. The surgical guide of claim 1, wherein the first portion is dimensioned to not cover an acetabular fossa when engaged to the acetabulum.

3. The surgical guide of claim 1, wherein the first portion defines an opening through the first portion at a location that, when the first portion is coupled to the acetabulum, corresponds to the location of an acetabular fossa.

4. The surgical guide of claim 1, wherein the patient-matched outer surface is configured to conform to the portion of the acetabulum in a single, predefined rotational orientation relative to the alignment axis.

5. The surgical guide of claim 4, wherein the patient-matched outer surface is configured to conform to a plurality of contours along the portion of the acetabulum when the first portion is placed within the acetabulum at a first orientation, and not conform to the plurality of contours when the first portion is positioned within the acetabulum at a second orientation; and
wherein the single, predefined rotational orientation corresponds with the first orientation.

6. The surgical guide of claim 1, wherein the second portion is detachable from the first portion and the second portion is configured to engage the first portion in a predefined orientation.

7. The surgical guide of claim 1, wherein the alignment portion includes a post defining a through hole along the alignment axis, and wherein the patient-matched outer surface extends along only a first region of a plurality of adjacent regions of the first outer surface.

8. The surgical guide of claim 7, wherein the depth-limiting feature is a patient-specific height of the post; and
wherein the depth-limiting feature is configured to engage an instrument to impede insertion of the guide rod beyond a patient-specific insertion depth, the patient-specific insertion depth being a depth that prevents the guide rod from protruding through a medial wall of the acetabulum of the particular patient.

9. The surgical guide of claim 1, wherein the second portion includes a second outer surface dimensioned to conform to a plurality of contours of an anatomy of the patient.

10. The surgical guide of claim 1, wherein the depth-limiting feature is dimensioned to limit insertion of the guide rod from protruding through a medial wall of the acetabulum of the particular patient.

11. The surgical guide of claim 1, wherein the patient-specific insertion depth permits a secure engagement of the guide rod with cortical bone of the acetabulum.

12. The surgical guide of claim 1, wherein the outer edge is circular shaped; and
wherein the slot extends from the outer edge toward a central location of the second outer surface to define a perimeter of the crescent-shaped planar surface.

13. The surgical guide of claim 1, wherein the outer edge comprises a convex outer edge portion that meets the first outer surface and a concave inner edge portion that defines the slot.

14. The surgical guide of claim 13, wherein the walls extend perpendicular from the second outer surface to the first outer surface.

15. The surgical guide of claim 1, wherein the first portion comprises a plurality of guide bores extending from the first outer surface to the second outer surface and configured to receive corresponding pins to secure the first portion to the acetabulum such that the patient-matched outer surface conforms to the portion of the acetabulum of the particular patient.

16. A surgical hip guide for a particular patient, the particular patient having an acetabulum with an attached ligamentum teres, the surgical hip guide comprising:
a modular alignment post; and
a patient-specific guide body having a patient-matched outer surface that conforms to at least an adjacent first portion of the acetabulum of the particular patient when the surgical hip guide is attached at a patient-specific and predetermined angular orientation within the acetabulum, the patient-matched outer surface having one or more side walls extending inwardly from a periphery and defining an aperture and a slot, the slot accommodates the attached ligamentum teres of the particular patient, the aperture configured to receive the modular alignment post, wherein the modular alignment post comprises:
an alignment portion defining an alignment axis such that when the surgical hip guide is coupled to the acetabulum, the alignment axis is oriented at a predetermined orientation relative to the acetabulum; and
a depth-limiting feature to limit insertion of a guide rod along the axis to a patient-specific insertion depth.

17. The surgical guide of claim 16, wherein the modular alignment post is positioned over an acetabular fossa when engaged to the acetabulum.

18. The surgical guide of claim 16, wherein the aperture is at a location that, when the patient matched outer surface is coupled to the acetabulum, corresponds to the location of an acetabular fossa.

19. The surgical guide of claim 16, wherein the patient-matched outer surface is dimensioned to mate with a plurality of different contours along an outer surface of the first portion of the acetabulum when the surgical hip guide is attached to the acetabulum at one, and only one, predefined angular orientation relative to the alignment axis.

20. The surgical guide of claim 16, wherein the depth-limiting feature is a patient-specific height of the modular alignment post; and
wherein the depth-limiting feature is configured to engage an instrument to impede insertion of the guide rod beyond the patient-specific insertion depth, the patient-specific insertion depth being a depth that prevents the guide rod from protruding through a medial wall of the acetabulum of the particular patient.

21. The surgical guide of claim 16, wherein the modular alignment post includes an end portion with a patient-matched surface that conforms to a plurality of mating contours along a portion of the particular patient's acetabulum.

22. The surgical guide of claim 16, wherein the patient-specific insertion depth permits a secure engagement of the guide rod with cortical bone of the acetabulum.

23. The surgical hip guide of claim 16, wherein the patient-specific guide body comprises a crescent-shaped planar surface that abuts a portion of the patient-matched outer surface at an outer edge; and
wherein the one or more sidewalls extend from the patient-matched outer surface to the crescent-shaped planar surface.

24. The surgical hip guide of claim 16, wherein the aperture is defined at an end of the slot.

25. A surgical hip guide for a particular patient, the particular patient having an acetabulum with an attached ligamentum teres, the surgical hip guide comprising:
a guide body having a patient-matched outer surface, a crescent-shaped surface, and one or more side walls, wherein the patient-matched outer surface conforms to at least a first portion of the acetabulum of the particular patient when the patient-matched outer surface is at one, and only one, of a plurality of positions within the acetabulum, the patient-matched outer surface comprises an outer convex edge shared with the crescent-shaped surface and a first inner concave edge shared with the one or more side walls, the one or more side walls extend from the first inner concave edge to a second inner concave edge shared with the crescent-shaped surface and define an aperture and a slot, the slot configured to accommodate the attached ligamentum teres of the particular patient; and an alignment post adapted to be positioned along an alignment axis and received by the aperture, the alignment post comprising a first end portion, a second end portion, and a post aperture, wherein at least one of the post aperture and the alignment axis is oriented pre-operatively based on patient-specific data of the particular patient.

26. The surgical guide of claim 25, wherein the alignment post is modular.

27. The surgical guide of claim 25, wherein, the first end portion is patient matched.

28. The surgical guide of claim 25, wherein the first end portion establishes a desired rotational position of the alignment post.

29. The surgical guide of claim 25, wherein the second end portion provides a depth-limiting feature.

30. The surgical guide of claim 25, wherein the alignment axis is in a predetermined orientation relative to the acetabulum when the guide body and the alignment post are coupled to the acetabulum.

31. The surgical guide of claim 25, wherein the post aperture is in a predetermined orientation relative to the acetabulum when the guide body and the alignment post are coupled to the acetabulum.

32. The surgical guide of claim 25, wherein the alignment post is custom fabricated for the particular patient to achieve a desired length.

33. The surgical guide of claim 25, wherein the alignment post is selected from at least one set of alignment posts with standard sizes and incrementally varying lengths.

* * * * *